Dec. 1, 1959 C. D. SIMONIAN ET AL Plant Pat. 1,882
PLUM TREE
Filed Oct. 10, 1958
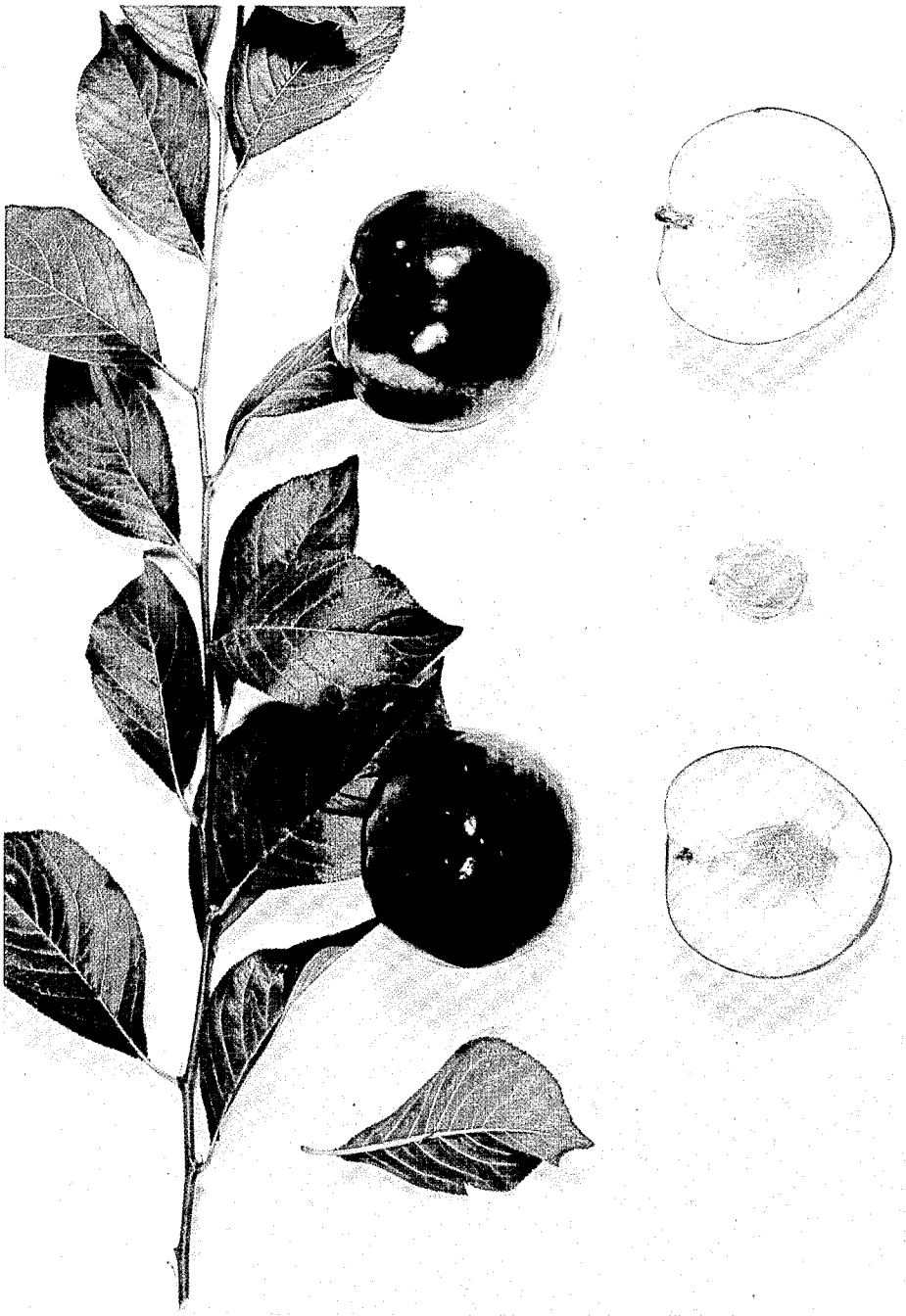
COCHE D. SIMONIAN
LUKE KAZARIAN
INVENTORS
HUEBNER & WORREL
ATTORNEYS
BY Richard M. Worrel United States Patent Office Plant Pat. 1,882
Patented Dec. 1, 1959

1,882

PLUM TREE

Coche D. Simonian and Luke Kazarian, Fowler, Calif.

Application October 10, 1958, Serial No. 766,637

1 Claim. (Cl. 47—62)

The present invention relates to a new and distinct variety of plum tree.

Several years ago, applicant Luke Kazarian, found and observed a seedling plum tree growing in his back yard at his home located at 318 North Fifth Street, in Fowler, California. Said applicant is unable to explain the presence of the tree and does not know its parentage but it appears to have been a chance seedling. He observed the tree carefully and took care of it over a period of many years. Mr. Kazarian believed that said plum tree was a new variety because of several distinctive characteristics which he noted and including the following: that the tree was substantially self-thinning, that the plum was freestone and sweet all the way through and thus was not tart next to the skin or the pit as is characteristic of many known plums, and that the plum could remain on the tree for protracted periods and even be retained after picking for substantial periods under normal environmental conditions without spoiling.

Subsequently, the applicant, Coche D. Simonian, with Mr. Kazarian's permission and also recognizing the distinctive characteristics of the plum, grafted scions of said plum tree onto four-hundred Mariana plum trees (unpatented), a commonly employed wild rootstock for plums. The grafting was performed and the resultant trees still grow at the Simonian ranch at 9020 South Fowler Avenue in Fowler, California. The grafts grew well and displayed the same characteristics as the seedling plum tree described above.

It is recognized that most known plums must be picked within a few days after becoming sufficiently colored for sales appeal or they become too ripe for shipment. This critical feature is a marked disadvantage. No delay in picking can be accommodated because of poor market conditions, scarcity of pickers, adverse weather conditions or other causes. It is also recognized that in eastern markets, the plum characteristics most desirable from a sales standpoint are size, color, and firmness.

The plum tree, illustrated in the accompanying drawing showing characteristic fruit and foilage of the tree as they prevail in the middle of July, has several very significant features. The fruit is highly and desirably colored, is rounded and unusually firm, and is quite large. The fruit may be picked immediately after it is well colored or it may hang on the tree for as much as about four weeks thereafter. This quality has previously been virtually unknown in commercial plum varieties. It is found that the fruit may be held in cold storage after picking for at least thirty days in prime condition. Additionally, it is a freestone plum.

The detailed description follows and the color terminology as employed is in accordance with the "Dictionary of Color" by Maerz and Paul, second edition, published in 1950.

Tree:

*Size.*—Medium.

*Vigor.*—Very vigorous and unusually hardy. The original tree discovered, as described above, has been transplanted several times with ease and without any noticeable effect on the tree.

*Figure and shape.*—Typical.

*Productivity.*—Heavy. However, the tree is self-thinning and does not require much auxiliary thinning. In this respect it may be similar to the unpatented Santa Rosa inasmuch as it is generally necessary to wait until the tree has finished self-thinning to perform additional or auxiliary thinning.

*Regularity of bearing.*—Uniform and consistent.

Trunk: Typical in size and surface characteristics.

Branches:

*Size.*—Medium.

*Surface character.*—Medium.

*Color.*—Plate 48–H–1.

*Lenticels.*—Normal.

Leaves:

*Size.*—Large.

*Length.*—Approximately 4¼ inches.

*Width.*—Approximately 2¼ inches.

*Shape.*—Approximately elliptic but with pointed apical ends.

*Color.*—Plate 24–L–7.

*Marginal form.*—Serrulate.

*Gladular characteristics.*—Usually two or three at or near the juncture of the leaf blade and the petiole.

*Veins.*—Pinnately net-veined.

*Petiole.*—Length of approximately ⅞″ and thickness of approximately 3/32″.

Flower Buds: Typical.

Flowers:

*Dates of bloom.*—Same as most other plums, namely, in the first part of April.

*Size.*—Small.

*Color.*—White.

Fruit:

*Maturity.*—Fruit begins to color after the first of July and matures sufficiently for packing for eastern shipment from California between July 15 and August 1. For local market, fruit can remain on the tree until about August 15.

*Size.*—Large. Even when the fruit grows in clusters, it is found to size well. The fruit is generally uniform, has an average axial diameter of 2¼ inches, an average transverse diameter in the suture plane 2 1/16 inches, and an average diameter transversely at right angles to the suture plane of approximately 2 3/16 inches.

*Form.*—Generally uniform and well rounded in contrast to the Nubiana (unpatented) which is flatter and is slightly asymmetrical about the suture plane.

*Suture.*—Visible although varying from shallow to a mere line and extended from the stem cavity to a position laterally adjacent to the apex. The suture is slightly offset from the apex but passes directly through the cavity. In other words, the suture plane is acutely angularly related to a plane containing the apex and the cavity.

*Ventril surface.*—Rounded.

*Stem cavity.*—Pronounced and substantially conically symmetrical.

*Base.*—Truncate.

*Apex.*—Pointed.

*Stem.*—Length of approximately ½″ and caliper of approximately 3/32″.

Skin:

Thickness.—Thin.

*Texture.*—Smooth.

*Tendency to crack.*—None noticed.

*Color.*—Plate 8–E–6 Rose Ebony, in the well colored portions of the mature fruit. In mature fruit the area circumscribing the cavity lacks the typical specks of plums but the remainder of the fruit has the characteristic yellow-greenish specks or dots. In skin coloring, the fruit is closest to the El Dorado and Nubiana (both unpatented) of the known plums.

*Bloom.*—Characteristic bluish or purplish which rubs off easily.

Flesh:

*Color.*—Plate 12–I–6, Powdered Gold, and is distinguished from the El Dorado.

*Color of pit well.*—Plate 7–L–10, Kettledrum Manzanito Moro Red+.

*Juice.*—Moderate.

*Flavor.*—Sweet and almost no tartness or acidity. In flavor, the fruit is most nearly similar to the Green Kelsey (unpatented) and is sweeter than the Santa Rosa.

*Aroma.*—Characteristic to mild.

*Texture.*—Typically fibrous but very firm. Does not bruise easily. Is most nearly like the Green Kelsey but unlike the El Dorado in texture.

*Fibers.*—Typical.

*Ripening.*—Uneven and non-uniform as to where ripening first occurs.

*Eating quality.*—Excellent.

Stone:

*Type.*—Freestone at full maturity.

*Fibers.*—Elongated.

*Size.*—In mature fruit, a major axis of approximately $1\frac{5}{32}''$, a minor axis in the suture plane of approximately $\frac{3}{4}''$, and a minor axis in a plane transverse to the suture plane of approximately $\frac{13}{32}''$.

*Form.*—Elliptic.

*Ridges.*—Slightly furrowed.

*Color.*—Plate 12–L–8, Antique.

*Splitting tendency.*—None observed.

Use: Fresh market both local and requiring shipping, storage for market, and canning.

*Keeping quality.*—Excellent.

*Shipping quality.*—Excellent.

Having thus described our new plum tree, we claim: A new and distinct variety of plum tree substantially as illustrated and described characterized by vigorous growth, a tendency to self-thinning, and large, firm, freestone fruit having highly colored Rose Ebony skin ripening from about July 15 to August 1 and being particularly characterized by an ability to remain on the tree in marketable condition for several weeks after coloring.

No references cited.